United States Patent
Robinson et al.

(10) Patent No.: US 7,623,906 B2
(45) Date of Patent: *Nov. 24, 2009

(54) DIFFUSE REFLECTANCE SPECTROSCOPY

(75) Inventors: M. Ries Robinson, Albuquerque, NM (US); Robert G. Messerschmidt, Albuquerque, NM (US)

(73) Assignee: InLight Solutions, Inc, Albuquerque, NM (US)

( * ) Notice: Subject to any disclaimer, the term of this patent is extended or adjusted under 35 U.S.C. 154(b) by 1037 days.

This patent is subject to a terminal disclaimer.

(21) Appl. No.: 10/292,109

(22) Filed: Nov. 12, 2002

(65) Prior Publication Data

US 2004/0092822 A1 May 13, 2004

(51) Int. Cl.
*A61B 6/00* (2006.01)
(52) U.S. Cl. ................................ 600/473; 600/316
(58) Field of Classification Search .............. 600/310, 600/322, 323, 344, 336, 340, 472–480, 316; 356/446; 250/339.11, 341.8
See application file for complete search history.

(56) References Cited

U.S. PATENT DOCUMENTS

| | | | |
|---|---|---|---|
| 3,508,830 A | 4/1970 | Hopkins et al. | 356/103 |
| 3,769,974 A | 11/1973 | Smart et al. | 128/2.05 P |
| 4,223,680 A * | 9/1980 | Jobsis | 600/324 |
| 4,655,225 A * | 4/1987 | Dahne et al. | 600/316 |
| 4,661,706 A * | 4/1987 | Messerschmidt et al. | 250/341.8 |
| 4,852,955 A | 8/1989 | Doyle et al. | 350/1.2 |
| 4,853,542 A | 8/1989 | Milosevic et al. | 250/353 |
| 4,859,064 A | 8/1989 | Messerschmidt et al. | 356/446 |
| 4,975,581 A | 12/1990 | Robinson et al. | 250/339 |
| 5,015,100 A | 5/1991 | Doyle | 356/445 |
| 5,019,715 A | 5/1991 | Sting et al. | 250/571 |
| 5,051,602 A | 9/1991 | Sting et al. | 250/571 |
| 5,224,478 A | 7/1993 | Sakai et al. | 128/633 |
| 5,355,880 A | 10/1994 | Thomas et al. | 128/633 |
| 5,379,764 A | 1/1995 | Barnes et al. | 128/633 |
| 5,452,723 A | 9/1995 | Wu et al. | 128/664 |
| 5,490,506 A * | 2/1996 | Takatani et al. | 600/309 |
| 5,533,509 A | 7/1996 | Koashi et al. | 128/633 |
| 5,636,633 A * | 6/1997 | Messerschmidt et al. | 600/368 |
| 5,830,132 A | 11/1998 | Robinson | 600/310 |
| 5,935,062 A * | 8/1999 | Messerschmidt et al. | 600/322 |
| 6,016,435 A | 1/2000 | Maruo et al. | 600/316 |

(Continued)

OTHER PUBLICATIONS

Korte, E.H. et al, Infrared Diffuse Reflectance Accessory for Local Analysis on Bulky Samples, *Applied Spectroscopy*, vol. 42, No. 1, Jan. 1988, pp. 38-43.

(Continued)

*Primary Examiner*—Long V Le
*Assistant Examiner*—Jacqueline Cheng
(74) *Attorney, Agent, or Firm*—InLight Solutions, Inc.; V. Gerald Grafe

(57) ABSTRACT

An improved method and apparatus for diffuse reflectance spectroscopy. A specular control device is provided that can discriminate between diffusely reflected light that is reflected from selected depths or layers within the tissue. The specular control device permits a spectroscopic analyzer to receive the diffusely reflected light that is reflected from, for example, a first layer or depth within the tissue, while preventing the remaining diffusely reflected light from reaching the spectroscopic analyzer. Furthermore, the specular control device may prevent the specularly reflected light (e.g. surface reflected light) from reaching the spectroscopic analyzer.

29 Claims, 15 Drawing Sheets

U.S. PATENT DOCUMENTS 6,230,034 B1 * 5/2001 Messerschmidt et al. .... 600/322
6,622,033 B2 * 9/2003 Messerschmidt et al. .... 600/316
6,636,759 B2 * 10/2003 Robinson .................... 600/475

OTHER PUBLICATIONS

Marbach, R. et al, "Optical Diffuse Reflectance Accessory for Measurements of Skin Tissue by Near-Infrared Spectroscopy," *Applied Optics*, vol. 34, No. 4, Feb. 1, 1995, pp. 610-621.

Marbach, Ralf, "Measurement Techniques for IR Spectroscopic Blood Glucose Determination," (1994) pp. 1-158.

McIntosh, Bruce C. et al, Paper No. 424, 16th Annual FACSS Conference, Oct. 1989.

* cited by examiner

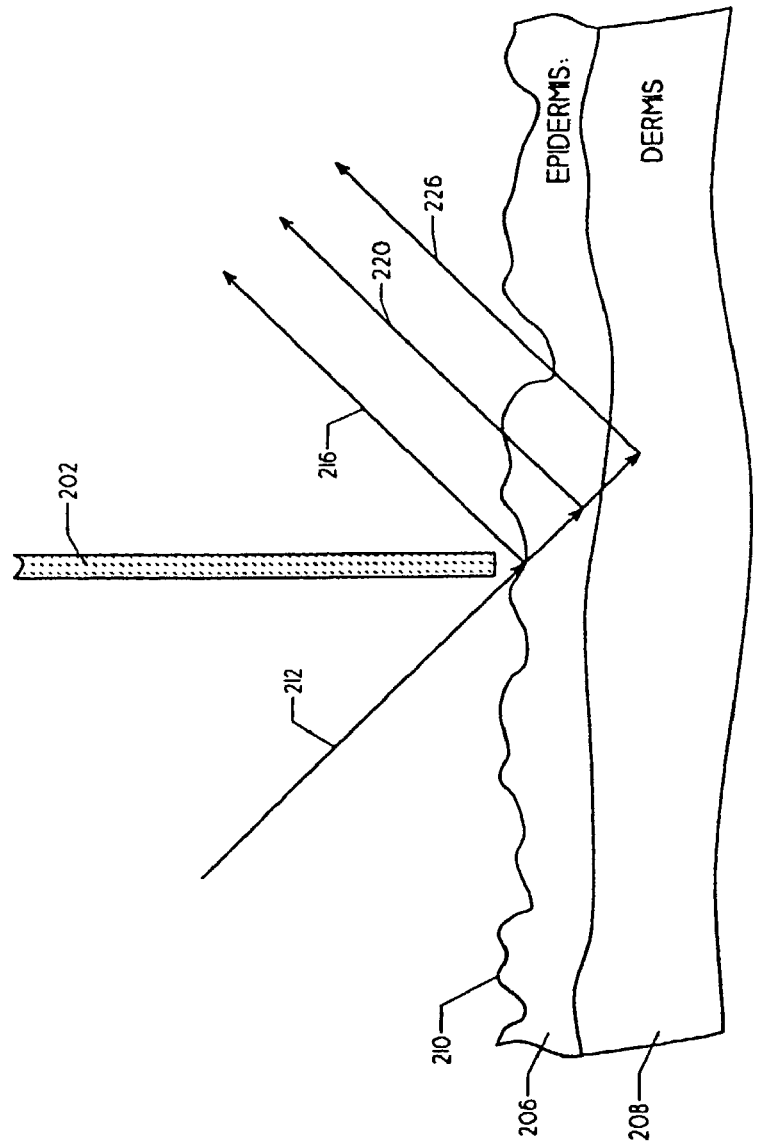

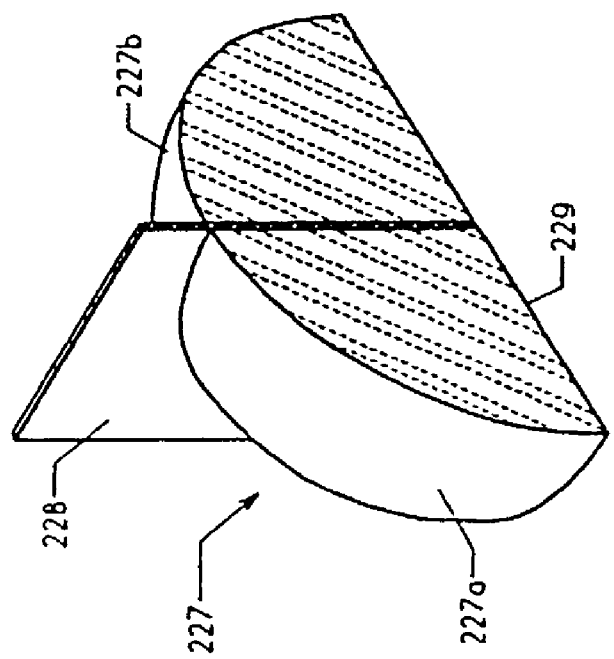
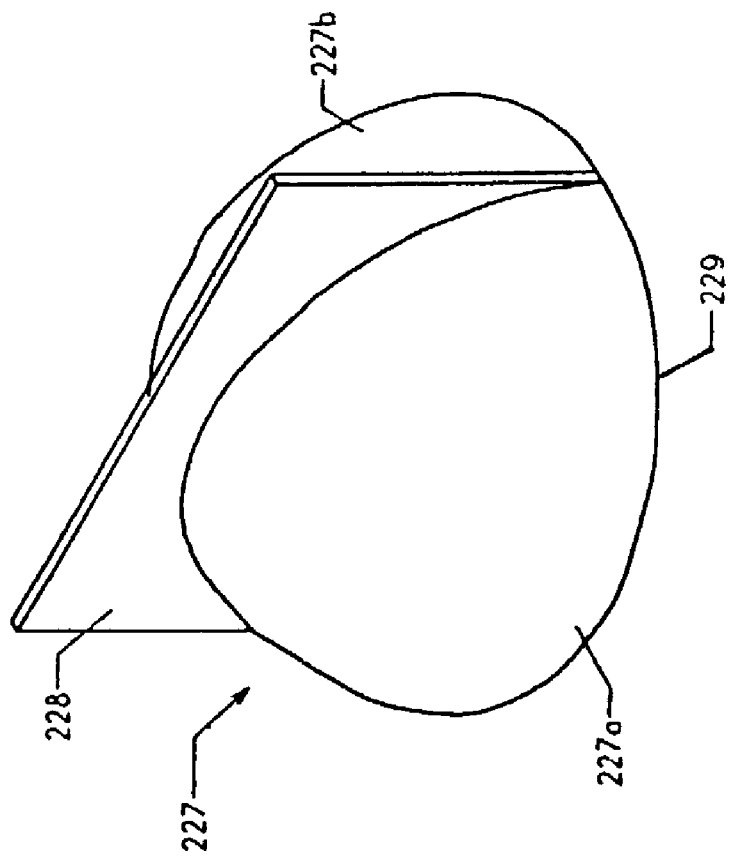
FIG. 11B
FIG. 11A

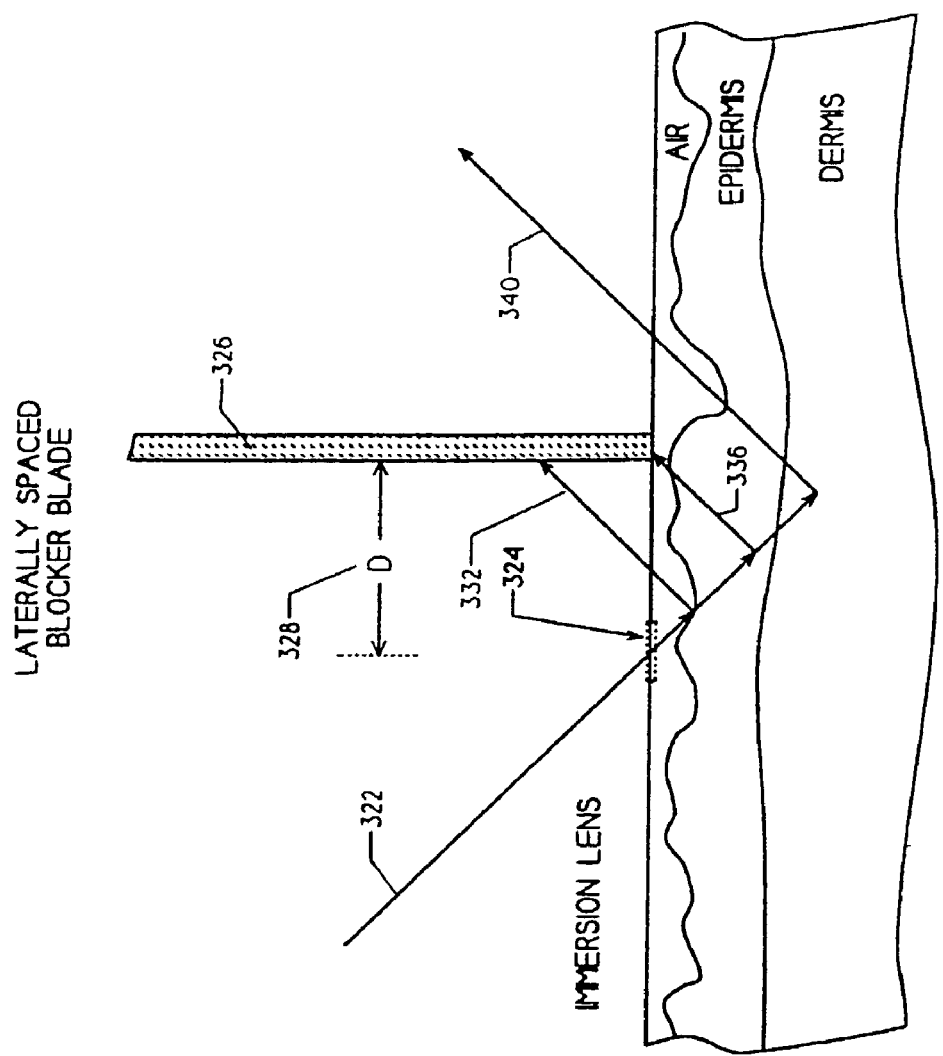

DIFFUSE REFLECTANCE SPECTROSCOPY

CROSS REFERENCES TO CO-PENDING APPLICATIONS

This application claims the benefit of U.S. patent application Ser. No 09/819,776, entitled "Improved Diffuse Reflectance Monitoring Apparatus," filed Mar. 28, 2001, which is a continuation of U.S. patent application Ser. No. 09/324,286, filed Jun. 2, 1999, now U.S. Pat. No. 6,230,034, which is a continuation of U.S. patent application Ser. No. 08/871,366, filed Jun. 9, 1997, now U.S. Pat. No. 5,935,062, which is a continuation-in-part of U.S. patent application Ser. No. 08/513,094, filed on Aug. 9, 1995, now U.S. Pat. No. 5,636,633, all of which are incorporated herein by reference.

FIELD OF THE INVENTION

The present invention relates generally to diffuse reflectance spectroscopy; and more particularly, to an improved method and apparatus for the spectroscopic measurement or analysis of biological attributes of tissue; and still more particularly, to an improved method and apparatus including a specular reflectance control device for use in such a measurement system.

BACKGROUND OF THE INVENTION

The need and demand for an accurate, non-invasive method for determining biological attributes of tissue is well documented. Accurate, non-invasive determination of blood glucose, as an example, could reduce many of the complications associated with diabetes. Similarly, accurate, noninvasive determination of various disease states could allow faster, more convenient screening and diagnosis, allowing more effective treatment.

Proposed non-invasive methods for determining biological attributes generally utilize quantitative infrared spectroscopy. Infrared spectroscopy measures the response of a substance to electromagnetic radiation (0.7-25 .mu.m) at various wavelengths. The response can be considered as derived from two categories, diffuse reflectance and specular reflectance. The specular reflectance of a sample is the light which does not propagate into the sample, but rather reflects from the front surface of the sample. This component contains information about the sample at the surface. If the material is homogeneous, this surface reflection can be related to the bulk. While the specular component does not physically appear much like an absorbance spectrum, it can be related to the absorbance spectrum of the bulk material through a transformation called the Kramers-Kronig transformation. The diffuse component is generally considered more useful for sample qualification and quantification than is the specular component. Various approaches have been proposed to emphasize the diffuse component relative to the specular component, but all suffer from shortcomings that limit their utility.

Accordingly, there is a need to improvements in spectroscopic technology that allow greater use of the diffuse component of a substance's response relative to the specular component.

SUMMARY OF THE INVENTION

The present invention provides a method and apparatus for improved measurement of diffusely reflected light. The present invention incorporates a specular control device that can discriminate between diffusely reflected light that is reflected from selected depths or layers within the tissue. The specular control device permits a spectroscopic analyzer to receive the diffusely reflected light that is reflected from, for example, a first layer or depth within the tissue, while preventing the remaining diffusely reflected light from reaching the spectroscopic analyzer. Furthermore, the specular control device may prevent the specularly reflected light (e.g. surface reflected light) from reaching the spectroscopic analyzer.

The specular control device can include an immersion lens that has a flat bottom surface and a semi-circular shaped top surface. The flat bottom surface can be positioned on the surface of tissue. A blocker blade is positioned within the immersion lens, and extends substantially perpendicular to the surface of the tissue sample. In a preferred embodiment, the blocker blade divides the immersion lens into approximately two equal halves, and extends downward to the flat bottom surface of the immersion lens. The blocker blade can be constructed to either reflect or absorb light having a wavelength in the range of the expected specularly and diffusely reflected light.

The incident light is directed to one of the two portions of the immersion lens. The blocker blade substantially prevents the incident light from traveling to the other half of the immersion lens. The immersion lens directs the incident light to the tissue sample, and in some embodiments, focuses the light on an illuminated spot on the surface of the tissue sample. A first portion of the incident light can be specularly reflected from the surface of the sample. A second portion of the light can enter the sample, and be diffusely reflected by the material within the sample. The diffusely reflected light is typically reflected at various depths within the sample.

The blocker blade can have two opposing surfaces including a front surface and a back surface, with a thickness defined therebetween. The thickness can be defined such that the blocker blade discriminates between light rays that are diffusely reflected from a first depth within the tissue from those light rays that are diffusely reflected from a second depth. The thickness of the blocker blade can depend, at least in part, on the angle of incidence and the spot size of the incident light rays on the tissue. The blocker blade can be sufficiently thick to substantially prevent those light rays that are diffusely reflected from a selected depth or layer within the sample from reaching the spectroscopic analyzer.

The present invention is particularly useful for obtaining a diffuse reflectance spectrum from human tissue for the non-invasive determination of biological attributes, such as, for example, the presence or concentration of glucose in blood or interstitial fluid, the presence or extent of glycosolated collagen, the presence or extent of glycosolation effects, the state of progression of a disease evidenced in the tissue response. Human skin typically includes an outer epidermis layer and an inner dermis layer. The epidermis layer contains very little or no blood, and thus the corresponding diffusely reflected light from the epidermis layer contains little or no information about many biological attributes. By preventing the diffusely reflected light from the epidermis layer from reaching the spectroscopic analyzer, an information rich spectrum from the dermis layer can be obtained and analyzed.

The back surface of the blocker blade can be laterally spaced a distance from the illuminated portion of the tissue sample such that the light rays that are diffusely reflected from the epidermis layer are substantially prevented from reaching the spectroscopic analyzer. The front surface of the blocker blade can be positioned directly adjacent the illuminated portion of the tissue sample, within the illuminated portion, or laterally spaced toward the back surface relative to the illuminated portion.

A thick blocker blade according to the present invention can substantially prevent the specularly reflected component of light from reaching the spectroscopic analyzer, even when the surface of the sample is not perfectly flat. One such sample is human skin. The surface of human skin is relatively rough and moderately rigid. A thick blocker blade according to the present invention can reduce the leakage of light between the surface of the skin and the blocker blade. This can improve the quality of the resulting spectrum that is provided to the spectroscopic analyzer.

The present invention also provides a method for obtaining a diffuse reflectance spectrum from human tissue for the non-invasive determination of biological attributes of tissue. The method comprises the steps of: (a) generating infrared energy; (b) directing the infrared energy to the tissue; and (c) collecting the infrared energy that is reflected from a first depth and rejecting the infrared energy that is reflected from a second depth.

BRIEF DESCRIPTION OF THE DRAWINGS

The drawings, which are not necessarily to scale, depict illustrative embodiments and are not intended to limit the scope of the invention.

FIG. 10 is a schematic drawing showing a "thin" blocker blade for mechanically discriminating against specular reflectance, in accordance with the prior art;

FIG. 11A is a perspective view of in illustrative specular control device in accordance with the present invention;

FIG. 11B is a cutaway view of the illustrative specular control device of FIG. 11A;

FIG. 15 is a simplified schematic drawing detailing an effectively "thick" blocker blade made from a single thin blocker blade that is laterally spaced from the illuminated spot of the incident light rays.

DETAILED DESCRIPTION OF THE INVENTION

Figure 1:
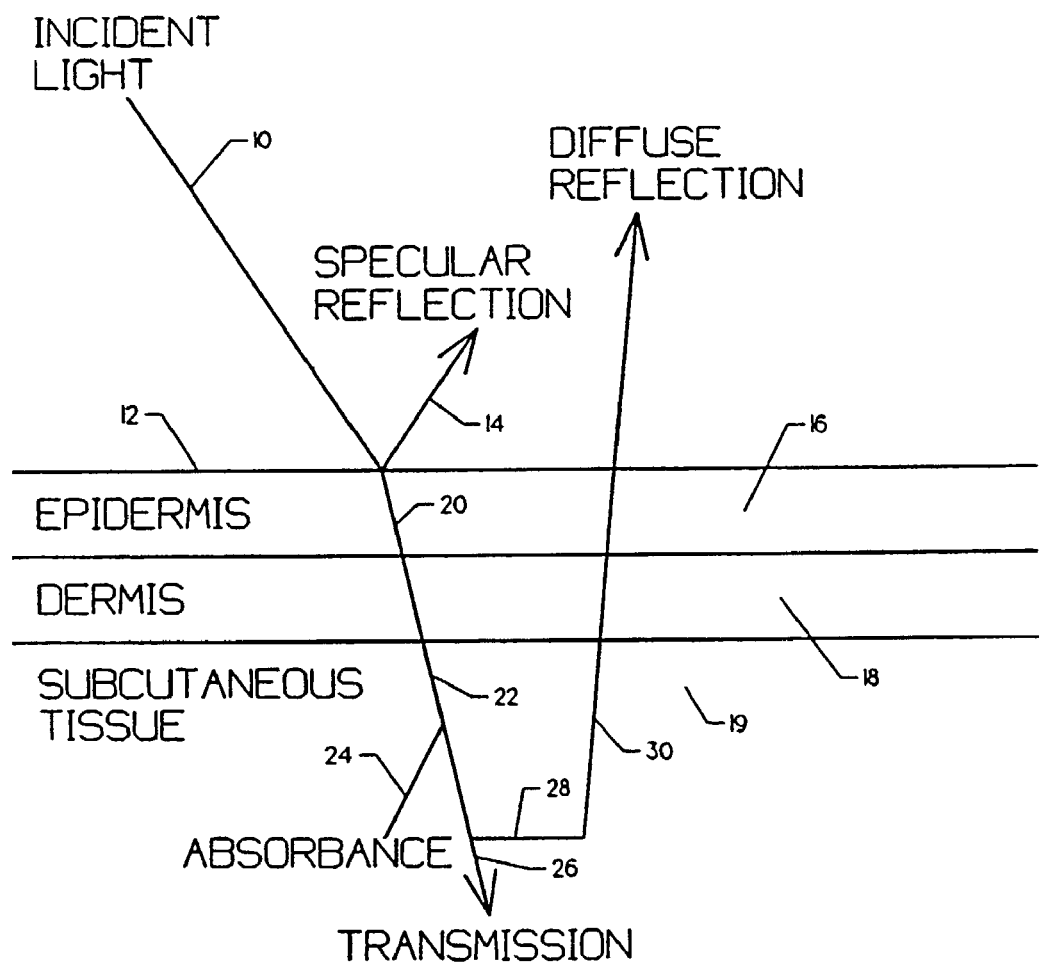
FIG. 1 is a simplified schematic showing the alternative responses to light incident on an analyte-containing tissue, including specular reflection, diffuse reflection, absorption and transmission.

FIG. 1 is a schematic representation of light energy incident on an analyte-containing tissue sample. A tissue sample 12 includes an upper layer or epidermis 16, a middle layer or dermis 18 and subcutaneous tissue 19. Incident light 10 illuminates the tissue sample 12, wherein portions of the light energy may be transmitted through the tissue sample, resulting in transmitted light 26 exiting the opposing side of the tissue sample. Alternatively, a tissue sample may absorb a portion of the light energy, resulting in absorbed light energy 24 as heat. A third phenomena includes specular reflection 14 of a portion of the incident light 10. Finally, a portion of the light energy can be diffusely reflected 30.

The diffusely reflected light 30 undergoes several refractions due to contact with the various components within the tissue sample. Eventually a portion of the diffusely reflected light energy 30 returns to the surface of the tissue sample 12 and exits back through the skin surface to the measuring device. Thus, both specular reflected light 14 and diffuse reflected light 30 combine and are directed back toward the instrument. Of the light directed toward the instrument, the diffusely reflected light 30 can contain desirable information concerning the biological attribute of interest. The specularly reflected light can contains information on the avascular epidermis, which can contain less or no information concerning the biological attribute of interest.

Problems associated with diffuse reflectance sampling of tissue can be reduced by the distribution of the input and output optics based on center symmetry. In a center symmetry configuration, the light rays 10 are focused onto the tissue sample 12 by an optical system, incorporating lenses. Light rays that are specularly reflected from the surface of the tissue 12 generally exit the optical system on the opposite side of the beam focus.

Figure 2:
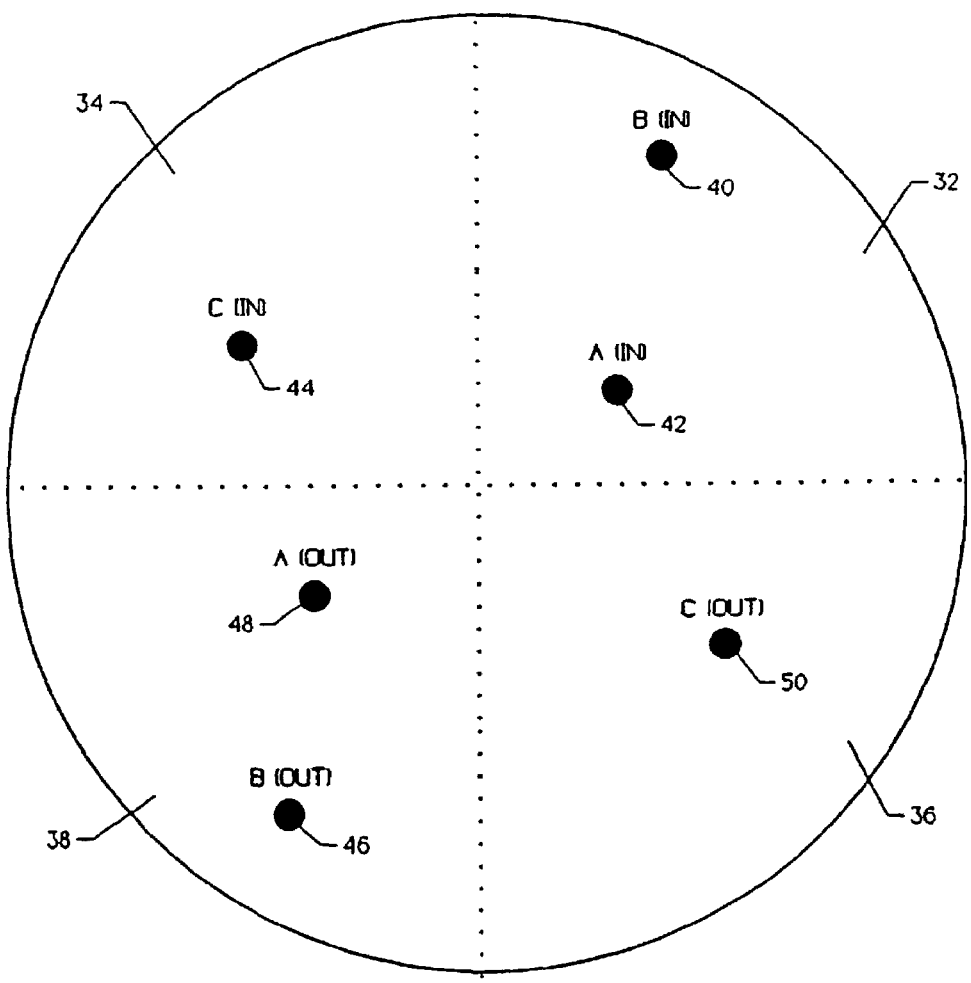
FIG. 2 is a schematic representation of the effect on specular reflectance utilizing input and output rays symmetric about a center focus.

FIG. 2 is a schematic diagram which illustrates the effect on light rays passing through the lens system. Light rays A, B, and C are depicted as passing through a generally circular transparent plate divided into four quadrants about the center point. The quadrants include first quadrant 32, second quadrant 34, third quadrant 38 and fourth quadrant 36. Input light energy A 42 is incident on and passes through the plate in the first quadrant. Due to center point symmetry, the output light energy A 48 due to specular reflectance returns through the plate in the third quadrant. Likewise, input light energy B 40 is also incident on the first quadrant 32. Output light energy B 46, which is the result of spectral reflectance exits the third quadrant 38. Similarly, input light energy C 44, which is incident on the second quadrant 34, has a component of specularly reflected light which exits from the fourth quadrant 36 as indicated as output light energy C 50.

Figure 3:
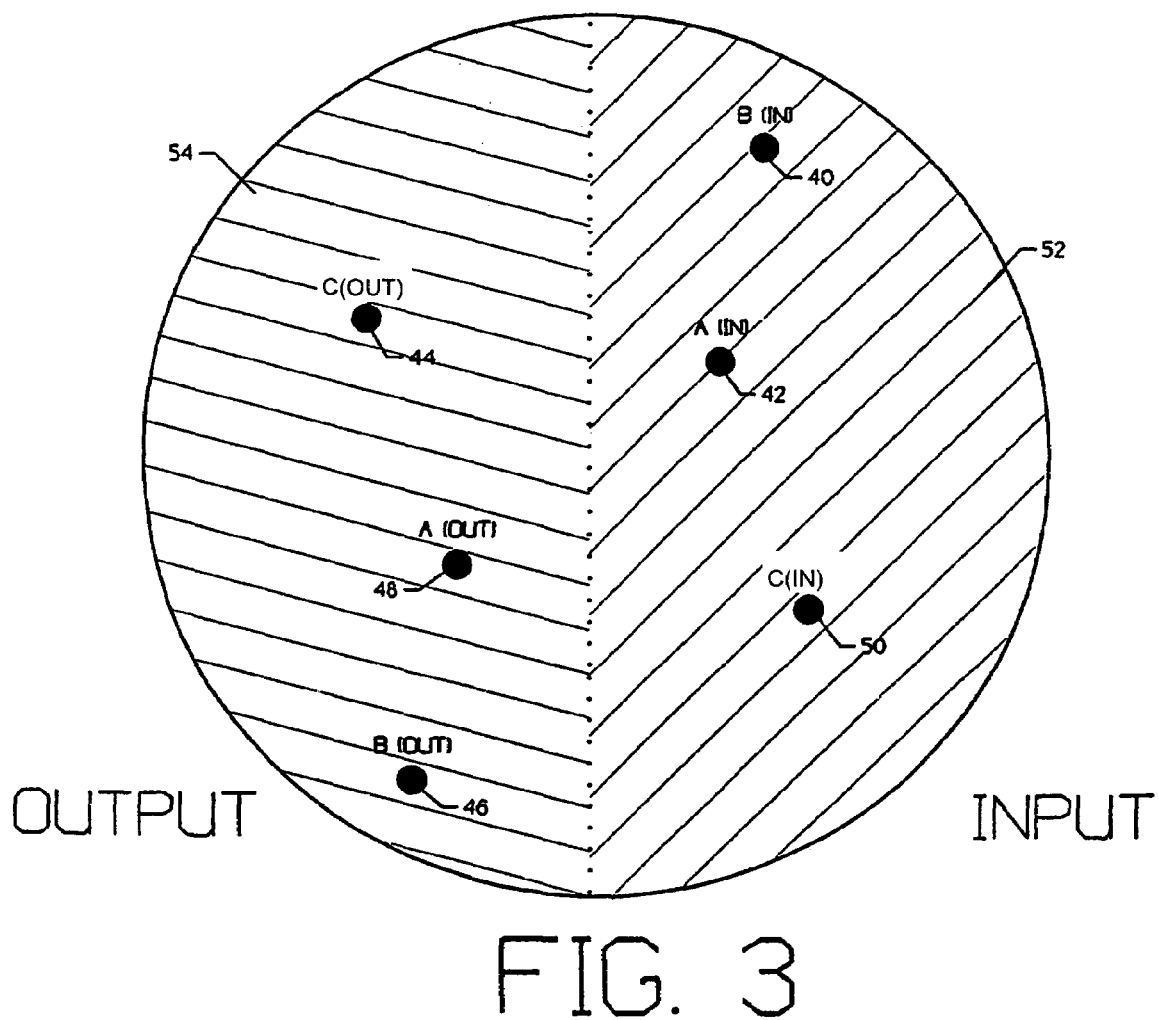
FIG. 3 depicts a typical single mirror optical configuration for reflectance sampling, wherein the optical beam is divided into an input and output side about a single center line.

In contrast to the concept of center point symmetry, a typical single mirror optical configuration for reflectance sampling includes an optical beam divided into an input and an output side about a single center line. FIG. 3 depicts this configuration. A generally circular plate having an input side 52 and an output side 54 is depicted. A center line divides the sides, passing through the diameter of the plate. Input rays A 42, B 40 and C 50, which pass through the plate, have specularly reflected components or output light energy A 48, B 46 and C 44, which are actually sampled by the output optics and will be seen by any detector.

Figure 4:
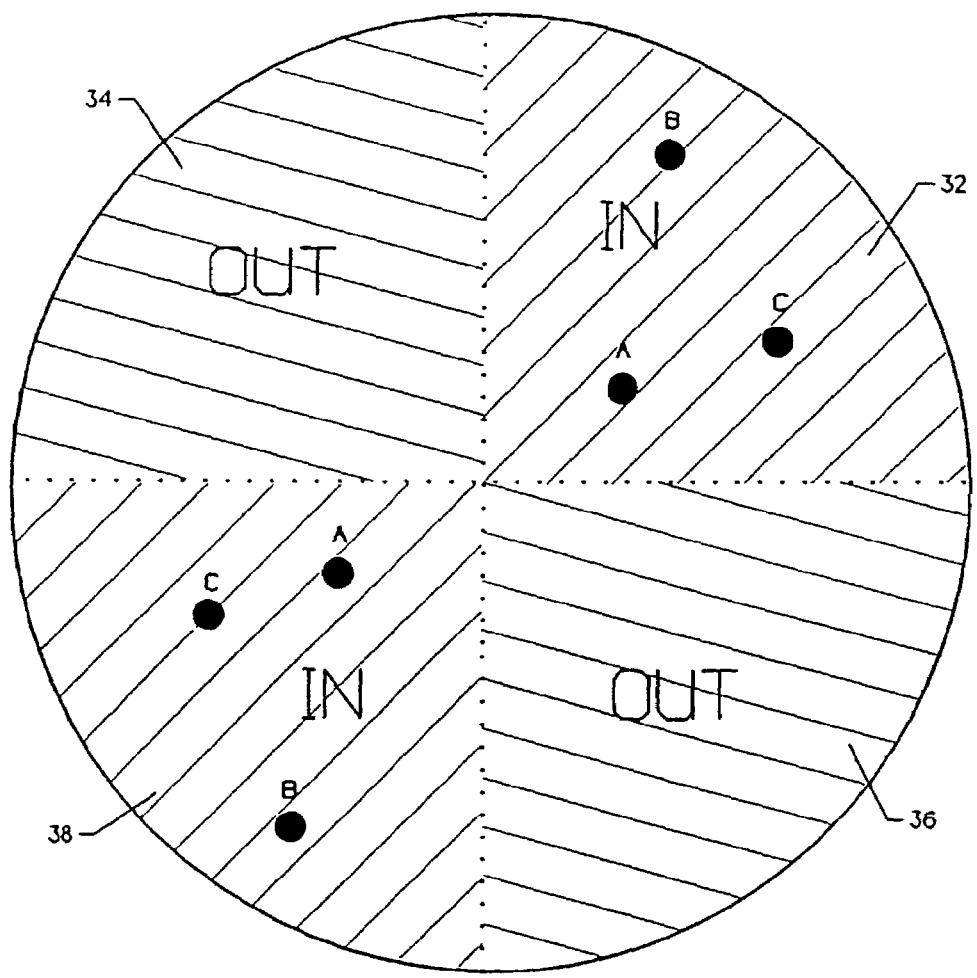
FIG. 4 is a schematic representation of the elimination of specularly reflected light utilizing four sections.

Problems associated with specular reflectance can be reduced by a specular control device incorporating the concepts of center point symmetry as depicted in FIG. 1 to overcome the problems with standard single mirror optical configurations for reflectance sampling. FIG. 4 depicts a generally circular plate divided into four quadrants. With the configuration of FIG. 4, the first quadrant 32 and third quadrant 38 are defined as input quadrants. The second quadrant 34 and fourth quadrant 36 are defined as output quadrants. With this embodiment, the light energy source is incident on the circular plate. However, the input quadrants allow the light energy to pass through, while the output quadrants are opaque. Thus, only light incident on the input quadrants passes through the specular control device to contact the tissue sample.

Light reflected from the tissue sample, including both specularly reflected light and diffusely reflected light is incident upon the opposite side of the specular control device. However, as explained for FIG. 1, all of the specularly reflected light returning from the tissue sample will be incident upon the first or third quadrants 32, 38 and will pass back through these openings. In contrast, a quantity of diffusely reflected light will be incident upon the second quadrant 34 and fourth quadrant 36 without any interfering specular reflection. The diffusely reflected light can then be reflected from the surface of the second and fourth quadrants 34, 36 and directed to the analyzer. In this way only the diffusely reflected light is analyzed.

Figure 5:
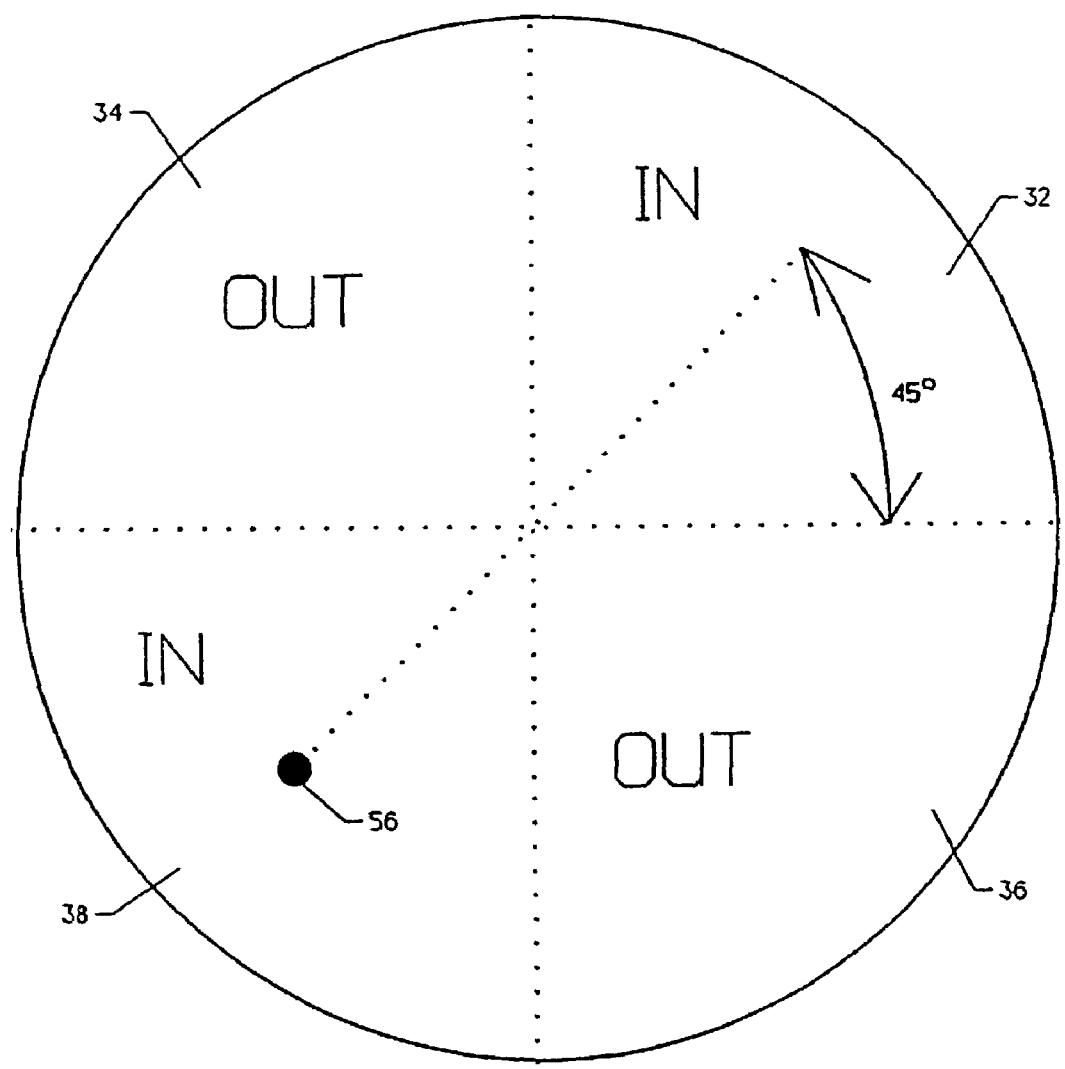
FIG. 5 is a schematic representation of directional change required for diffuse reflected light energy to reach the analyzer.
Figure 6:
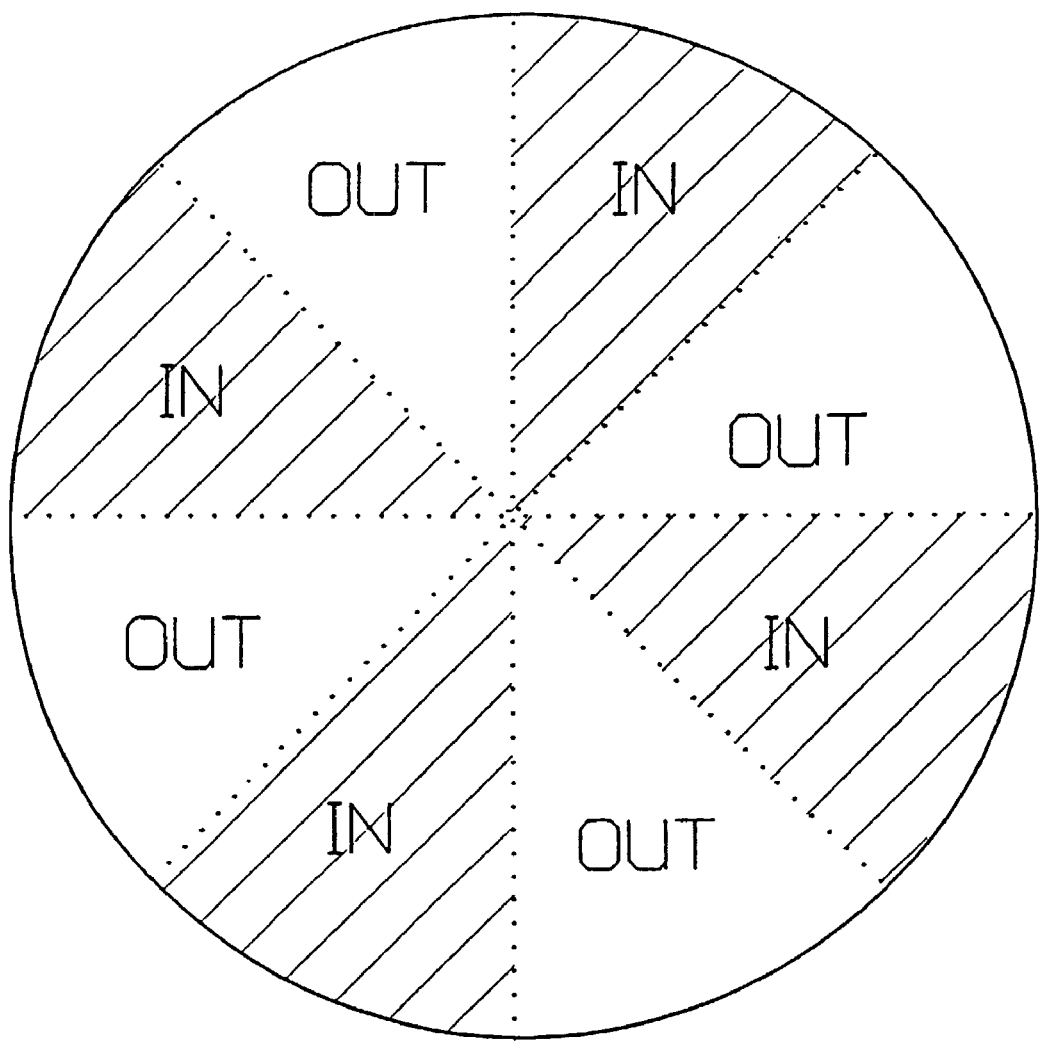
FIG. 6 is a schematic representation of a specular control device incorporating eight sections.
Figure 7:
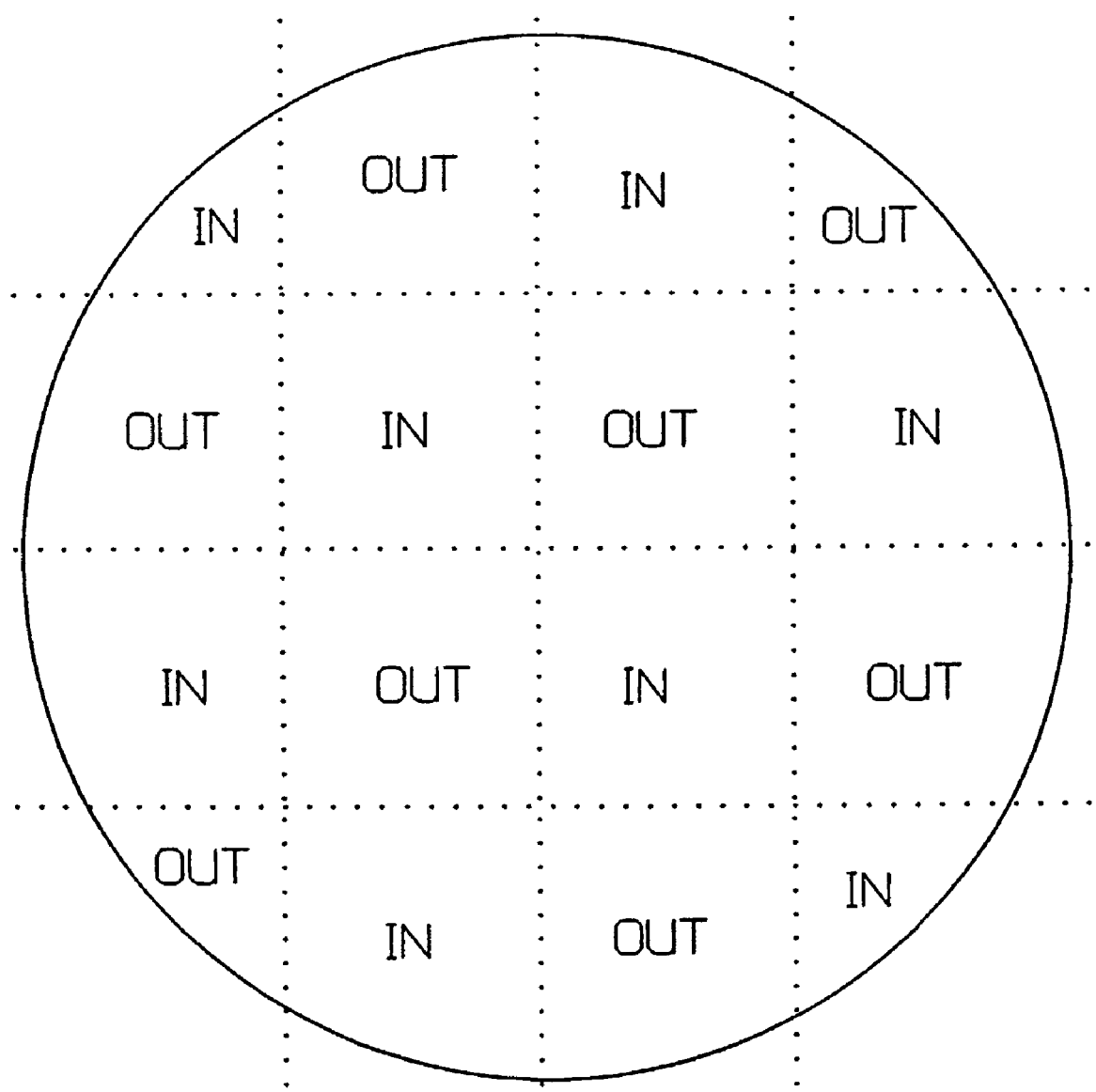
FIG. 7 is a schematic diagram of an alternative specular control device utilizing generally rectangular symmetric sections.

As shown in FIG. 5, the diffusely reflected portion of a light ray 56 would have to undergo a change in direction of at least 45 degrees before it could be collected by the output optics. The number of photons which would successfully complete this directional change without absorbance will be less than those that can successfully undergo a smaller directional change. The efficiency of the optical system can be improved by further dividing the optical beam into numerous symmetrically based input and output sections. FIG. 6 depicts one such alternative embodiment. In FIG. 6, the optical beam is divided into eight separate wedge shaped quadrants about the center point. In the eight quadrant configuration, a light ray located in the center of an input quadrant would have to undergo a directional change of only 22.5 degrees. The number of quadrants can be further increased. Alternatively, as depicted in FIG. 7, the optical beam can be divided into 16 generally square quadrants which are also symmetrical about the center point.

Figure 8A:
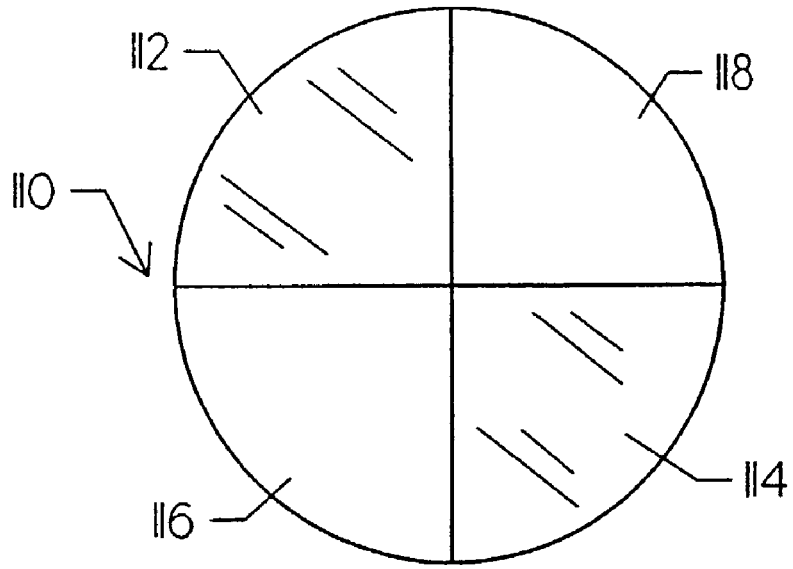
FIG. 8A is a plan view of a first embodiment of the specular control device.

FIG. 8A discloses a specular control device indicated generally at 110. The surface of specular control device 110 is divided into an even numbered plurality of sections, here shown as open sections 116 and 118, and reflective sections 112 and 114. Open sections 116 and 118 are intended to pass or transmit any beam of light that is incident to the surface of specular control device 110. In contrast, reflecting sections 112 and 114 are intended to block the incident beam and reflect portions of it to a predetermined site.

In the embodiment of FIG. 8A, each of sections 112, 114, 116 and 118 are of equal size and thus the total surface area of the open sections 116 and 118 is equal to the total surface area of reflecting sections 112 and 114. Further, each of reflecting sections 112 and 114 is situated between a pair of open sections 116 and 118; and, similarly, each of open sections 116 and 118 is located between a pair of reflecting sections 112 and 114. Finally, each reflecting section such as 112 is opposite to another reflecting section such as 114; and, each open section such as 116 is opposite to another open section such as 118.

Figure 8B:
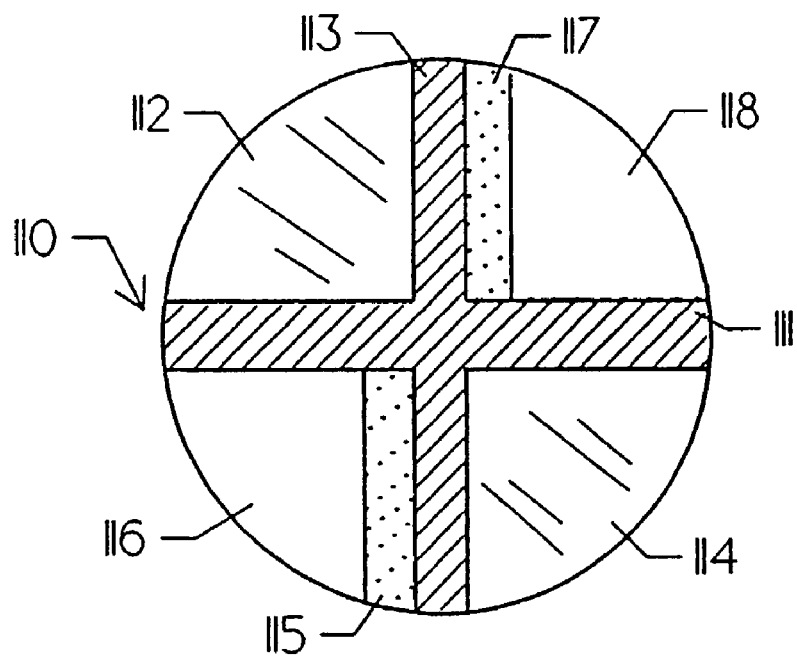
FIG. 8B is a plan view of a second embodiment of the specular control device.

FIG. 8B depicts another embodiment of the apparatus of FIG. 8A. In FIG. 8B, specular control device 110 is again divided into a plurality of reflecting sections 112 and 114, and open sections 116 and 118. Each reflecting section such as 112 and 114 is situated between a pair of open sections 116 and 118, and similarly each of open sections 116 and 118 is situated between a pair of reflecting sections such as 112 and 114. Each reflecting section is opposite to another reflecting section, and each open section is opposite to another open section.

FIG. 8B also shows a set of opaque spacers 113 and 111 located along the borders between each of sections 112, 116, 114 and 118. Spacers 111 and 113 encourage a more precise definition between the analytical beam sent to illuminate a sample and the data beam reflected from the sample. The opaque spacing between the reflecting and open sections achieves this desired improvement by, for example, discouraging cross talk in the various adjacent sections from transmitted and reflected light beams.

When opaque spacers 111 and 113 are utilized along the diameters of a circular specular control device surface such as 110, they result in equal division of the remaining surface area between reflecting sections 112 and 114 and open sections 116 and 118. As it can be desirable for the analysis of certain samples to have the reflecting sections surface area unequal to the open sections surface area, this is shown accomplished in FIG. 8B by the addition of opaque spacers 115 and 117. For purposes of description, opaque area 115 has been shown as added to opaque spacer 113 to decrease the surface area of open section 116; and, similarly, opaque area 117 has been added to opaque spacer 113 to decrease the surface area of open section 118.

In the embodiment shown in FIG. 8B, in a system where the source analytical beam is transmitted through open areas 116 and 118, and the diffuse reflection from a sample is reflected by sections 112 and 114 to a detector the addition of opaque sections 115 and 117 can decrease the percentage of the source beam which illuminates the sample.

Figure 9:
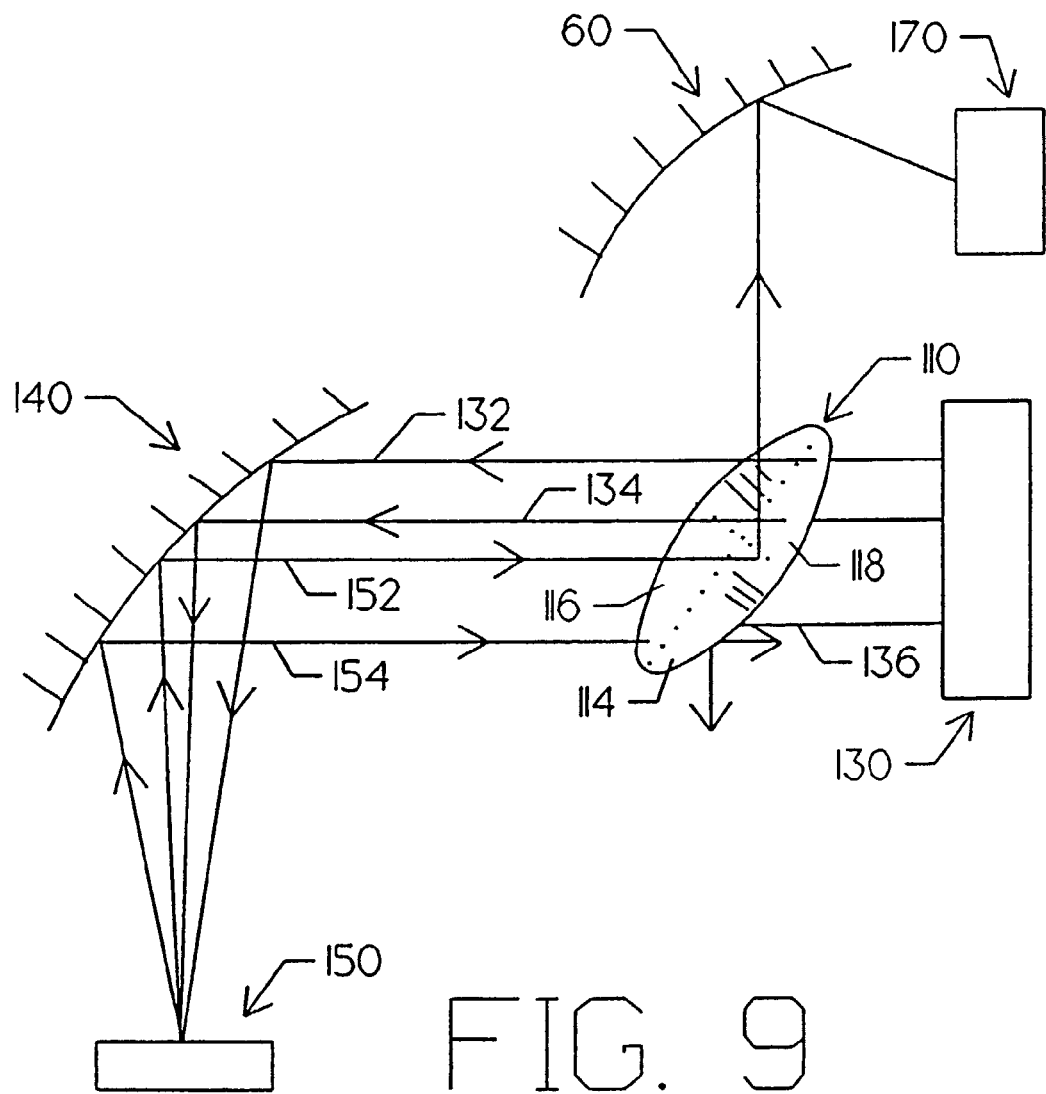
FIG. 9 is a schematic drawing showing the use of the specular control device of this invention in a spectroscopy system.

FIG. 9 is a schematic of a diffuse reflectance spectroscopy system utilizing the apparatus of this invention. A specular control device 110 has open area 118 and reflective area 114. Specular control device 110 need not be of a circular configuration as shown in FIGS. 8A and 8B but could be, for example, elliptical or rectangular in shape.

A light or energy source 130 provides an analytical source beam indicated at 132, 134 and 136. Source beam 132, 134 and 136 impinges on a first surface of specular control device 110. That portion of the source beam indicated at 136 is incident to reflecting portion 114 of specular control device 110 and is reflected away as shown by the arrow. That portion of the source beam indicated at 132 and 134 passes through open area 118 of specular control device 110, and continues on to be reflected by an elliptical mirror 140 to a desired focus on sample 150.

A diffuse reflectance beam 152 is reflected from sample 150 to mirror 140 and thence to the reflective surface 114 as shown by the arrows. Diffusely reflected beam 152 is reflected onto an elliptical mirror 60 from which it is focused into a detector 170.

In contrast to the diffusely reflected beam 152, a specularly reflected beam of light 154 is represented in FIG. 9. As is shown in FIG. 9, the specularly reflected beam 154 is reflected from the sample 150 to the mirror 140. This specularly reflected beam then passes through the open area 116 which is the open quadrant opposing the input quadrant 118 through which that light beam entered. The specularly reflected light 154 is thus not reflected to the analyzer 170 as described above for the diffusely reflected beam 152.

In FIG. 9, specular control device 110 can be a single element having the reflective and open sections as shown in FIGS. 8A and 8B. Or, should it be desirable for manufacturing purposes, specular control device 110 can be a unit of a desired thickness having a first and second surface, each of which surface is treated in the same manner shown in FIGS. 8A and 8B. The reflecting and open sections on a first surface would be directly opposite the reflecting and open surfaces on a second surface to achieve the desired results.

FIG. 10 is a schematic drawing showing a "thin" blocker blade for mechanically discriminating against specular reflectance, in accordance with U.S. Pat. No. 4,661,706, issued Apr. 28, 1987, to Messerschmidt et al. Messerschmidt et al. demonstrate that the specular and the diffuse component of reflected light can be separated mechanically, taking advantage of the fact that the specular component emanates from the surface of the sample. A blade-like device, or blocker 202, "skims" the specular light before it can impinge on the detector. Messerschmidt et al. teach that a "thin" blocker 202 is essential to maximize the efficiency of the system, and minimizing the distortion of the output spectrum. More particularly, Messerschmidt et al. state that to obtain the maximum efficiency and the closest approximation to the Kubelka-Munk relationship, a thin blocker device 202 should be used having a thickness that is a fraction of the optical depth of the sample. A thicker blocker, Messerschmidt et al. explain, will remove energy that penetrates only a short distance into the sample before reflecting, and thus may have a catastrophic effect on the efficiency when used with a sample having a shallow optical depth.

Messerschmidt et al. also state that a thick blocker may introduce spectral distortions caused by energy that is once reflected by the sample to the lower surface of the blocker and again reflected from the blocker to the sample before energy escapes from the far side of the blocker. This is problematic, according to Messerschmidt et al., because the energy reflected from the lower surface of the blocker will acquire the reflectance spectral features of the blocker itself and thus distort the output spectrum.

The "thin" blocker approach of Messerschmidt et al. suffers from a number of limitations, some of which are discussed below. First, the "thin" blocker blade 202 does not provide any discrimination between the diffusely reflected energy that is reflected from various depths within the sample. That is, the thin blocker 202 does not provide any discrimination between the diffusely reflected light 220 reflected from a top layer and the diffusely reflected light 226 reflected from a lower layer, as shown. This limitation is of particular importance when the tissue sample is layered or otherwise non-homogeneous, and only a selected set of the layers contain the desired information. This occurs in many applications including the non-invasive measurement of blood analytes, such as glucose, using the diffuse reflectance spectrum reflected therefrom. For example, it is known that human skin has an outer epidermis layer 206 and a dermis layer 208. The epidermis layer 206 contains very little or no blood, and thus the corresponding diffusely reflected light 220 reflected from the epidermis layer 206 typically contains little or no glucose information. Applicants have discovered that the diffusely reflected light 220 from the epidermis layer 206 only contaminates the desired output spectrum 226 of the information rich dermis layer 208.

In addition to the above, the "thin" blocker 202 of Messerschmidt et al. may not perfectly conform to the rough surface 210 of the tissue sample. This can cause locations where the light 212 effectively leaks or pipes under the blocker 202 without interacting with the sample, thereby further contaminating the resulting output spectrum. This is shown explicitly by light ray 216.

FIG. 11A is a perspective view of in illustrative specular control device in accordance with the present invention. FIG. 11B is a cutaway view of the same. The specular control device includes an immersion lens 227 that has a flat bottom surface 229 and a semi-circular shaped top surface. The flat bottom surface 229 is positioned on the surface of the tissue sample (not shown). A blocker blade 228 is positioned within the immersion lens, and extends substantially perpendicular to the surface of the tissue sample. The blocker blade 228 may divide the immersion lens into approximately two equal halves 227a and 227b, and extends downward to the flat bottom surface 229 of the immersion lens 227. The blocker blade 228 is constructed to either reflect or absorb light having a wavelength in the range of the expected specularly and diffusely reflected light.

The incident light is directed to one of the two equal halves ("equal halves", or just "portions"?) 227a, 227b of the immersion lens 227. The blocker blade 228 substantially prevents the incident light from traveling to the other half of the immersion lens 227. The immersion lens 227 directs the incident light to the tissue sample, and in some embodiments, focuses the light on an illuminated spot (see FIG. 15) on the surface of the tissue sample. A first portion of the incident light will typically be specularly reflected from the surface of the sample. A second portion of the light will typically enter the sample, and be diffusely reflected by the material within the sample. The diffusely reflected light is typically reflected by material that is at various depths within the sample.

Figure 12:
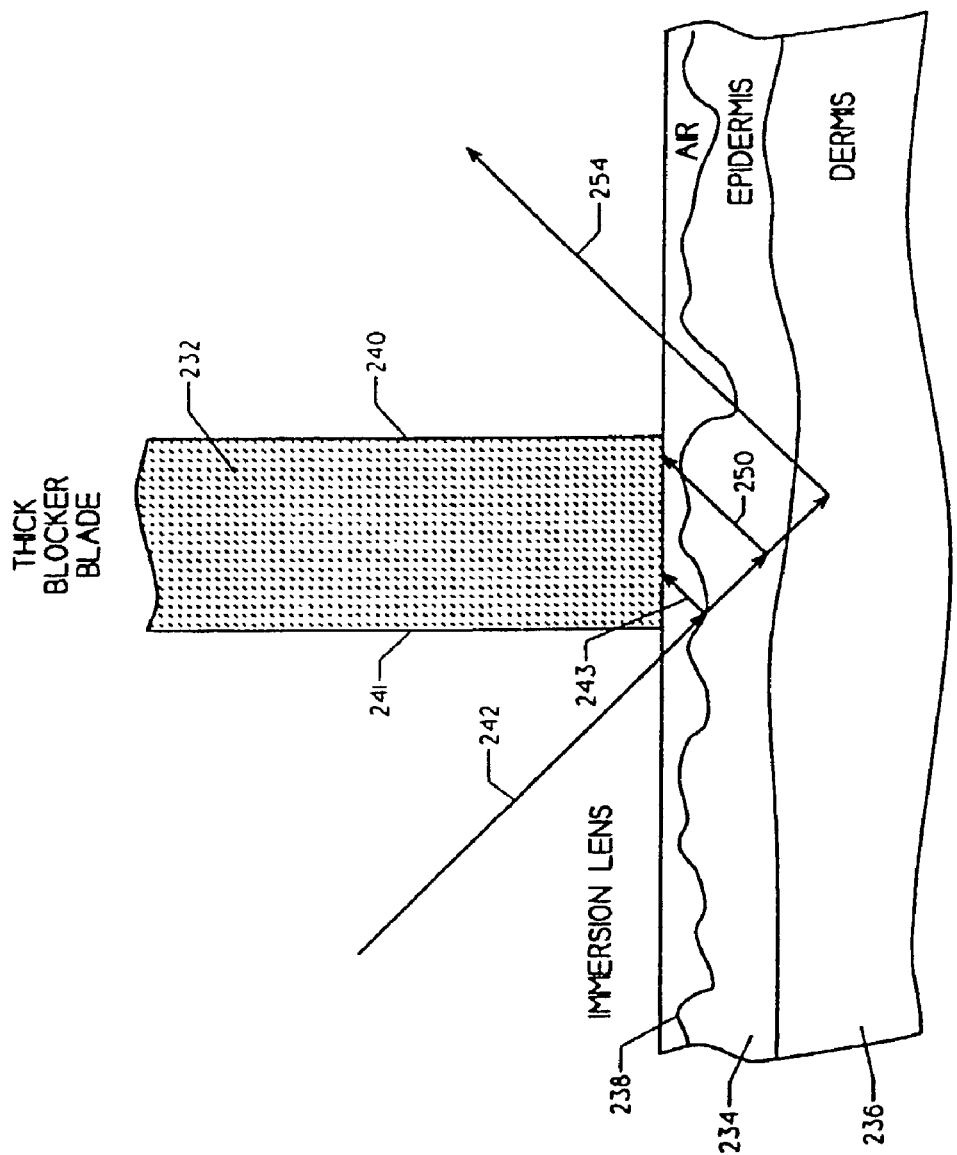
FIG. 12 is a simplified schematic drawing detailing the "thick" blocker blade of the present invention.

FIG. 12 is a simplified schematic drawing detailing the "thick" blocker blade of the present invention. The immersion lens is positioned adjacent the top surface 238 of a tissue sample. In the illustrative diagram, the tissue sample is human skin having an outer epidermis layer 234 and an inner dermis layer 236. Because the top surface 238 of the tissue sample is rough, gaps will typically be present between at least parts of the immersion lens and the top surface 238 of the tissue sample as shown.

In accordance with the present invention, a relatively thick blocker blade 232 is provided. The blocker blade 232 has a back surface 240 and a front surface 241, with a thickness defined therebetween. The tissue sample may include a number of layers, including an epidermis layer 234 and a dermis layer 236. Applicants have discovered that it is desirable to exclude the diffusely reflected light rays that are reflected by the epidermis layer.

The back surface 240 of the blocker blade 232 can be laterally spaced a distance from the illuminated portion of the tissue sample such that the light rays 250 that are diffusely reflected from the epidermis layer 234 are substantially prevented from reaching the spectroscopic analyzer. As indicated above, the epidermis layer 234 can have little or no blood therein, and thus the diffusely reflected light from the epidermis layer 234 tends to contaminate the desired spectrum of the diffusely reflected light 254 from the information rich dermis layer 236. By preventing the diffusely reflected light 250 of the epidermis layer 234 from reaching the spectroscopic analyzer, a contaminated spectrum from the dermis layer 236 can be obtained and analyzed. The front surface 241 of the blocker blade 232 may be positioned directly adjacent the illuminated portion of the tissue sample, within the illuminated portion, or laterally spaced toward the back surface 240 relative to the illuminated portion.

The epidermis layer is typically about 40 micrometers to about 400 micrometers in thickness at desired sample areas. A blocker blade thickness for these applications can be 100 micrometers to 800 micrometers, for example 400 micrometers.

In addition to the above, a thick blocker blade 232 according to the present invention can substantially prevent the specularly reflected component 243 from reaching the spectroscopic analyzer, even when the surface of the sample is not perfectly flat. Because the present invention provides a thick blocker blade 232, the leakage of light between the surface of the skin 238 and the blocker blade 232 may be reduced or eliminated. This can improve the quality of the resulting spectrum that is provided to the spectroscopic analyzer.

A method according to the present invention for obtaining a diffuse reflectance spectrum from human tissue for the non-invasive determination of biological attributes of tissue comprises the steps of: (a) generating infrared energy; (b) directing the infrared energy to the tissue; and (c) collecting the infrared energy that is reflected from a first depth and rejecting the infrared energy that is reflected from a second depth.

Figure 13:
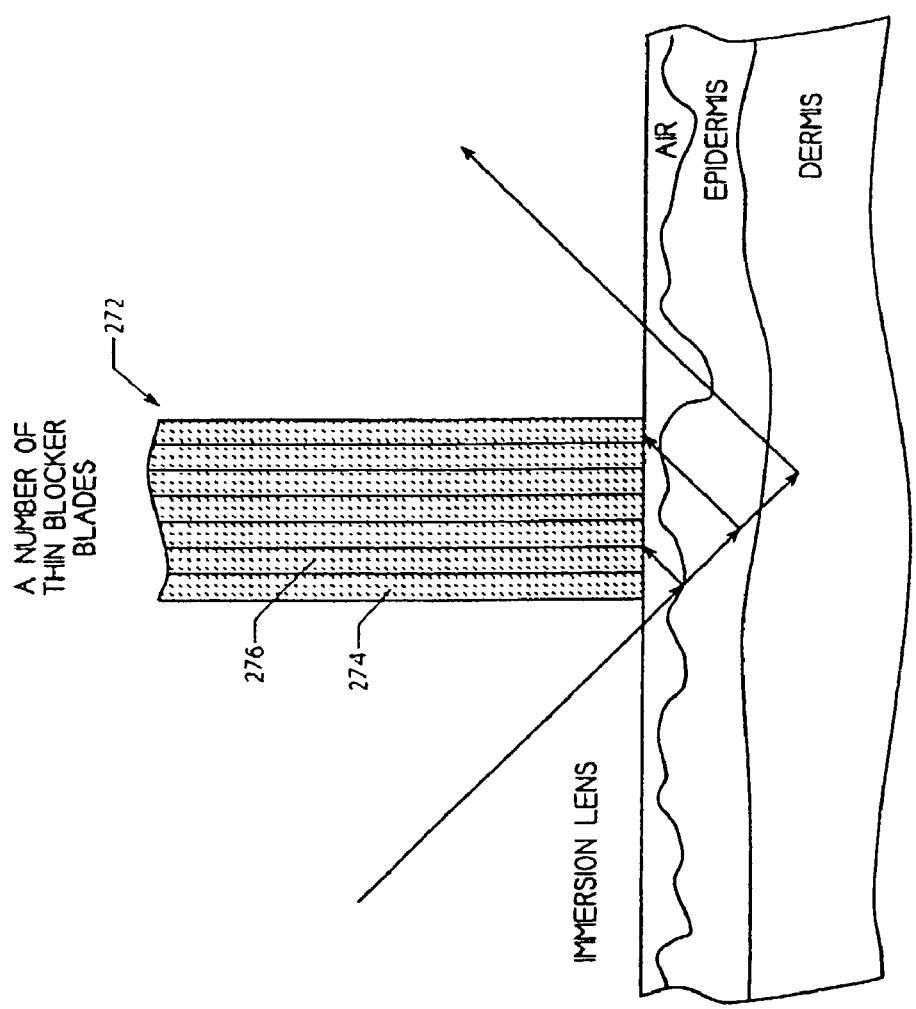
FIG. 13 is a simplified schematic drawing detailing the "thick" blocker blade of the present invention, made from a number of abutting thin blocker blades.

FIG. 13 is a simplified schematic drawing detailing the "thick" blocker blade of the present invention, made from a number of abutting thin blocker blades. Rather than forming the blocker blade 272 from a single homogeneous material, it is contemplated that a number of thin blocker blades, for example thin blocker blades 274, 276, may be used to form blocker blade 272.

Figure 14:
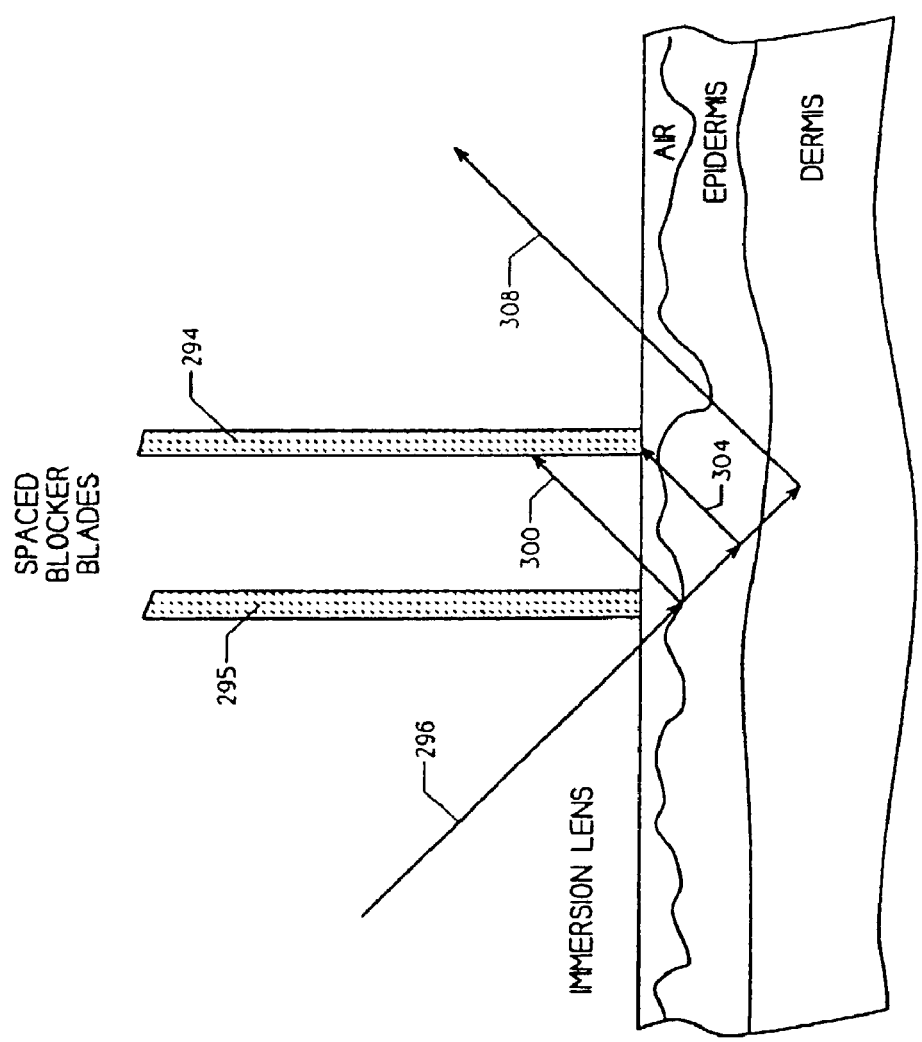
FIG. 14 is a simplified schematic drawing detailing an effectively "thick" blocker blade made from two spaced thin blocker blades.

FIG. 14 is a simplified schematic drawing detailing an effectively "thick" blocker blade made from two spaced thin blocker blades 294 and 295. In this illustrative embodiment, the front blocker blade 295 is used to confine the incident light 296 to the left portion of the immersion lens. The back blocker blade 294 can prevent both specularly reflected light 300, and any diffusely reflected light 304 that is reflected from the epidermis layer, from reaching the spectroscopic analyzer.

FIG. 15 is a simplified schematic drawing detailing an effectively "thick" blocker blade made from a single thin blocker blade that is laterally spaced from the illuminated spot of the incident light rays. As indicated above, the immersion lens may focus the incident light onto an illuminated spot 324. In this embodiment, no front blocker blade is needed to confine the incident light to the left portion of the immersion lens. Thus only one blocker blade is used, which is spaced a sufficient distance "D" 328 from the illuminated spot 324 to prevent both specularly reflected light 332 and any diffusely reflected light 336 provided by the epidermis layer, from reaching the spectroscopic analyzer.

Those skilled in the art will recognize that the present invention can be manifested in a variety of forms other than the specific embodiments described and contemplated herein. Accordingly, departures in form and detail can be made without departing from the scope and spirit of the present invention as described in the appended claims.

What we claim is:

1. An apparatus for obtaining a diffuse reflectance spectrum from tissue, comprising:
   a. a generator for generating infrared energy at a plurality of wavelengths;
   b. a director for directing said infrared energy to said tissue;
   c. a collector for collecting infrared energy that is reflected by said tissue, wherein said collector collects infrared energy at each of the plurality of wavelengths;
   d. a discriminator for discriminating between infrared energy that is diffusely reflected from a first depth within said tissue from infrared energy that is diffusely reflected from a second depth within said tissue, said discriminator specifically sized for substantially preventing said infrared energy that is diffusely reflected from the first depth from reaching said collector.

2. The apparatus of claim 1 wherein said discriminator means comprises a blocker blade adapted to be positioned on or adjacent to a surface of said tissue.

3. The apparatus of claim 2 wherein said blocker blade is adapted to extend substantially perpendicular to the surface of said tissue, and has two opposing surfaces including a front surface and a back surface defining a thickness thereof.

4. The apparatus of claim 3 wherein said director directs said infrared energy to form an illuminated portion of the surface of said tissue.

5. The apparatus of claim 4 wherein the back surface of said blocker blade is laterally spaced a predetermined distance from said illuminated portion of said tissue such that infrared energy that is diffusely reflected from the first depth within said tissue is substantially prevented from reaching said collecting means.

6. The apparatus of claim 5 wherein the front surface of said blocker blade is adjacent to said illuminated portion of said tissue.

7. The apparatus of claim 3 wherein said blocker blade thickness defined by said front surface and said back surface is sufficient to prevent infrared energy that is diffusely reflected from the first depth from reaching said collector.

8. The apparatus of claim 3 wherein said blocker blade absorbs diffusely reflected infrared energy incident thereon.

9. The apparatus of claim 1, wherein the first depth corresponds to an epidermis layer of said tissue, and wherein the second depth corresponds to a dermis layer of said tissue.

10. The apparatus of claim 1, wherein said discriminator comprises a blocker blade having a thickness great enough to prevent light from leaking under the discriminator due to the roughness of said tissue top surface.

11. An apparatus for obtaining a diffuse reflectance spectrum from human tissue, comprising:
   a. a generator for generating infrared energy at each of a plurality of wavelengths;
   b. a director for directing said infrared energy to said tissue;
   c. a collector for collecting infrared energy that is reflected by said tissue, wherein said collector collects infrared energy at each of the plurality of wavelengths; and
   d. a discriminator for discriminating between infrared energy that is diffusely reflected from a first selected depth within said tissue from infrared energy that is diffusely reflected from a second selected depth, said discriminator specifically sized for substantially preventing said infrared energy that is diffusely reflected from said first selected depth from reaching said collector; and
   e. said discriminator comprises a blocker blade adapted to be positioned on or adjacent to the surface of said tissue, said director including an immersion lens, with said blocker blade positioned within said immersion lens.

12. A method for obtaining a diffuse reflectance spectrum from human skin tissue for the non-invasive determination of a biological attribute thereof, the human skin tissue having an epidermis layer and a dermis layer, the method comprising the steps of:
   a. generating infrared energy at each of a first plurality of wavelengths;
   b. directing said infrared energy to said tissue;
   c. collecting infrared energy at each of the plurality of wavelengths that is reflected from the dermis layer while discouraging the collection of infrared energy that is reflected from the epidermis layer with a discriminating means; and d. determining the biological attribute by analyzing the collected infrared energy.

13. The method of claim 12 wherein the directing step directs said infrared energy to a top surface of said tissue.

14. The method of claim 12, wherein directing the infrared energy to a said tissue comprises directing infrared energy to a first location on said tissue, and wherein collecting the infrared energy comprises collecting the infrared energy at a second location on said tissue. wherein only infrared energy that is reflected from the dermis layer is present at the second location.

15. A method as in claim 12, wherein the biological attribute is an analyte concentration, a disease state, or a tissue characteristic.

16. A method as in claim 12, wherein the biological attribute is an indication of diabetes or impaired glucose tolerance.

17. An apparatus for obtaining a diffuse reflectance spectrum from skin tissue, the skin tissue having an epidermis layer and a dermis layer, the apparatus comprising:

a. a source of infrared energy at each of a plurality of wavelengths for generating and delivering infrared energy to a first location on the skin tissue;

b. a collector for collecting infrared energy at each of the first plurality of wavelengths reflected from the dermis layer at a second location;

c. a discriminator for causing the collector to collect primarily the infrared light that is reflected from the dermis layer.

18. An apparatus as in claim 17, wherein the discriminator for causing the collector to collect primarily only the infrared energy that is reflected from the dermis layer is positioned between the infrared energy source and the collector.

19. An apparatus as in claim 18, wherein the discriminator for causing the collector to collect primarily only the infrared energy that is reflected from the dermis layer comprises a blocker.

20. An apparatus as in claim 19, wherein the blocker comprises a plate.

21. An apparatus as in claim 20, wherein the plate comprises a material opaque to infrared energy.

22. An apparatus as in claim 20, wherein the plate includes a front surface and a back surface, and wherein the back surface is laterally spaced from an illumination location to block infrared energy that is reflected from the epidermis layer.

23. An apparatus as in claim 22, wherein the front surface is positioned adjacent the illumination location.

24. An apparatus as in claim 22, wherein the front surface is laterally spaced from the illumination location.

25. An apparatus as in claim 22, wherein the plate is solid between the front surface and the back surface.

26. An apparatus as in claim 22, wherein the plate is not solid between the front surface and the back surface.

27. An apparatus as in claim 20, wherein the plate has a thickness, the infrared energy has a wavelength, and the thickness is greater than the wavelength.

28. An apparatus as in claim 27, wherein the thickness is greater than or equal to 100 micrometers.

29. An apparatus as in claim 27, wherein the thickness is 100 micrometers to 800 micrometers.

* * * * *